US006458540B1

(12) United States Patent
Ramberg

(10) Patent No.: US 6,458,540 B1
(45) Date of Patent: Oct. 1, 2002

(54) METHODS AND COMPOSITIONS FOR DETECTION OF SPECIFIC NUCLEOTIDE SEQUENCES

(75) Inventor: Elliot R. Ramberg, Hollywood, FL (US)

(73) Assignee: CyGene, Inc., Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/633,848

(22) Filed: Aug. 7, 2000

Related U.S. Application Data

(63) Continuation of application No. 09/313,121, filed on May 17, 1999, now Pat. No. 6,100,040, which is a continuation of application No. 08/739,069, filed on Oct. 25, 1996, now Pat. No. 5,962,225.
(60) Provisional application No. 60/005,938, filed on Oct. 27, 1995.

(51) Int. Cl.[7] .......................... C12Q 1/68; C12P 19/34; C07H 21/04
(52) U.S. Cl. .................. 435/6; 435/5; 435/91.2; 536/24.3; 536/24.31; 536/24.32
(58) Field of Search .................... 435/6, 5, 91.2; 536/24.3, 24.31, 24.32

(56) References Cited

U.S. PATENT DOCUMENTS

| | | | |
|---|---|---|---|
| 4,683,195 A | 7/1987 | Mullis et al. | 435/6 |
| 4,683,202 A | 7/1987 | Mullis | 435/91 |
| 4,775,619 A | 10/1988 | Urdea | 435/6 |
| 4,978,749 A | 12/1990 | Stratis et al. | 435/6 |
| 5,176,996 A | 1/1993 | Hogan et al. | 435/6 |
| 5,258,506 A | 11/1993 | Urdea et al. | 435/6 |
| 5,273,881 A | 12/1993 | Sena et al. | 435/6 |
| 5,422,251 A | 6/1995 | Fresco | 435/6 |
| 5,482,836 A | 1/1996 | Cantor et al. | 435/6 |
| 5,518,901 A | 5/1996 | Murtagh | 435/91.2 |
| 5,583,032 A | 12/1996 | Torrence et al. | 435/240.2 |
| 5,607,924 A | 3/1997 | Magda et al. | 514/44 |
| 5,639,609 A | 6/1997 | Kruse-Mueller et al. | 435/6 |
| 5,677,289 A | 10/1997 | Torrence et al. | 514/74 |
| 5,693,471 A | 12/1997 | Fresco | 435/6 |
| 5,714,328 A | 2/1998 | Magda et al. | 435/6 |
| 5,726,297 A | 3/1998 | Gryaznov et al. | 536/22.1 |
| 5,834,198 A | 11/1998 | Famulok et al. | 435/6 |
| 5,837,835 A | 11/1998 | Gryaznov et al. | 536/23.1 |
| 5,871,911 A | 2/1999 | Dahlberg et al. | 435/6 |
| 5,962,225 A | 10/1999 | Ramberg | 435/6 |
| 6,100,040 A | 8/2000 | Ramberg | 435/6 |

FOREIGN PATENT DOCUMENTS

EP  0 492 570 A1  12/1991
WO  WO 97 15691  5/1997

OTHER PUBLICATIONS

Actor et al., "A Bioluminescent Assay Using AquaLite for RT–PCR Amplified RNA from Mouse Lung", *The Journal of NIH Research*, vol. 8, p. 62 (Oct. 1996).

(List continued on next page.)

*Primary Examiner*—Carla J. Myers
(74) *Attorney, Agent, or Firm*—Kilpatrick Stockton

(57) ABSTRACT

Methods and compositions are provided for the detection of specific nucleic acid sequences purified from cellular or tissue sources. More particularly, the present invention includes methods and compositions for the detection of nucleic acid sequences using a protection molecule that forms a protected nucleic acid sequence (PNAS) such as a triplex or duplex nucleic acid structure that includes the target nucleic acid sequence. An assay using the methods of the present invention may include one, two or three levels of specificity to minimize false positive signals. An assay using the methods or compositions of the present invention can be performed on large amounts of purified DNA in a single test, with high levels of sensitivity, thus eliminating the need for DNA amplification procedures.

18 Claims, 1 Drawing Sheet

OTHER PUBLICATIONS

Atlas et al., "Tracking Microorganisms and Genes in the Environment", Environmental Biotechnology, Gilbert S. Omenn, eds, pp. 31–45 (1988).

Aviv et al., "Purification of Biologically Active Globin Messenger RNA by Chromatography on Oligothymidylic acid–Cellulose", Proc. Nat. Acad. Sci., vol. 69, No. 6, pp. 1408–1412 (Jun. 1972).

Berger et al., editors, "Guide to Molecular Cloning Techniques: Methods in Enzymology", vol. 152, pp. 612–613, 625–626.

Blume et al., "Triple helix formation by purine–rich oligonucleotides, targeted to the human dihydrofolate reductase promotor", Nucleic Acids Research, vol. 20, No. 7, pp. 1777–1784.

Cassiday et al., "Replica Plating of Colonies from Listeria––Selective Agars to Blood Agar to Improve the Isolation of Listeria monocytogenes from Foods", Applied and Environmental Microbiology, vol. 56, No. 7, Jul., pp. 2274–2275 (1990).

Chambers, Henry "Coagulase–Negative Staphylococci Resistant to β–Latam Antibiotics in vivo Produce Penicillin–Binding Protein 2A", Antimicrobial Agents and Chemotherapy, vol. 13, No. 12, pp. 1919–1924 (Dec. 1987).

Chirgwin et al., "Isolation of Biologically Active Ribonucleic Acid from Sources Enriched in Ribonuclease", Biochemistry, vol. 18, No. 24, pp. 5294–5299 (1979).

Chomczynski et al., "Single–Step Method of RNA Isolation by Acid Guanidium Thiocyanate–Phenol–Chloroform Extraction", Analytical Biochemistry, vol. 162, pp. 156–159 (1987).

Dhingra et al., "Hybridization Protection Assay: A Rapid, Sensitive, and Specific Method for Detection of Philadelphia Chromosome–Positive Leukemias", Blood, vol. 77, No. 2, pp. 238–242 (Jan. 15, 1991).

Favolaro et al., "Transcription Maps of Polyoma Virus–Specific RNA: Analysis by Two–Dimensional Nuclease S1 Gel Mapping", Methods in Enzymology, vol. 65, pp. 718–749.

Francois et al., "Sequence–Specific Recognition and Cleavage of Duplex DNA via Triple–Helix Formation by Oligonucleotides Covalently Linked to a Phenanthroline–Copper Chelate", PNAS USA, vol. 86, pp. 9702–9706 (Dec. 1, 1989).

Gillespie, David "The magic and challenge of DNA probes as diagnostic reagents", Veterinary Microbiology, vol. 24, pp. 217–233 (1990).

Goodwin, Graham H., "The analysis of sequence–specific DNA–binding proteins in cell extracts", Gel Electrophoresis of Nucleic Acids—A Practical Approach, Second Edition, Oxford University Press, pp. 225–247 (1990).

Guatelli et al., "Isothermal, in vitro amplification of nucleic acids by a multienzyme reaction modeled after retroviral replication", Proc. Natl., Acad. Sci., vol. 87, pp. 1874–1878 (Mar. 1990).

Kolberg et al., "The specificity of pilin DNA sequences for the detection of pathogenic Neisseria", Molecular and Cellular Probes, vol. 3, pp. 59–72 (1989).

Kwoh et al., "Transcription–based amplification system and detection of amplified human immunodeficiency virus type 1 with a bead–based sandwich hybridization format", Proc. Natl. Acad. Sci., vol. 86, pp. 1173–1177 (Feb. 1989).

Landegren et al., "DNA Diagnostics–Molecular Techniques and Automation,", Science, vol. 242, pp. 229–237, (Oct. 14, 1988).

Lee et al., "Poly(pyrimidine)· poly(purine) synthetic DNAs containing 5–methylcytosine form stable triplexes at neutral pH", Nucleic Acids Research, vol. 12, No. 16, pp. 6603–6614 (1984).

Lee et al., "Isolation of DNA from Fungal Mycelia and Single Spores", PCR Protocols: A Guide to Methods and Applications, Academic Press, Inc., pp. 282–287 (1990).

Lewis, Ricky "GEN's 10 Best Biotechnology Research Areas", Genetic Engineering News, vol. 10:1, p. 24 (1990).

Lizardi et al., "Exponential Amplification of Recombinant––RNA Hybridization Probes", Bio/Technology, vol. 6, pp. 1197–1202 (Oct. 1988).

Moser et al., "Sequence–Specific Cleavage of Double Helical DNA by Triple Helix Formation", Science, vol. 238, pp. 645–650 (Oct. 30, 1987).

Palmiter, Richard D., "Magnesium Precipitation of Ribonucleoprotein Complexes, Expedient Techniques for the Isolation of Undegraded Polysomers and Messenger Ribonucleic Acid", Biochemistry, vol. 13, No. 17, pp. 3606–3615 (1974).

Povsic et al., "Triple Helix Formation by Oligonucleotides on DNA Extended to the Physiological pH Range", Journal of the American Chemical Society, vol. 111, pp. 3059–2061 (Jan. 1, 1989).

Reddy et al, "Bacterial RNA Isolation with One Hour Centrifugation in a Table–Top Ultracentrifuge", Bio Techniques, vol. 8, No. 3, pp. 250–251 (1990).

Summers, William C., "A Simple Method for Extraction of RNA from E. coli Utilizing Diethyl Pyrocarbonate", Analytical Biochemistry, "Short Communications", vol. 33, No. 2, pp. 459–463 (1970).

Urdea et al., "A novel method for the rapid detection of specific nucleotide sequences in crude biological samples without blotting or radioactivity; application to the analysis of hepatitis B virus in human serum", Gene, vol. 61, pp. 253–264 (1987).

Wu et al., "The Ligation Amplification Reaction (LAR)–Amplification of Specific DNA Sequences Using Sequential Rounds of Template–Dependent Ligation", Genomics, vol. 4, pp. 560–569 (1989).

METHODS AND COMPOSITIONS FOR DETECTION OF SPECIFIC NUCLEOTIDE SEQUENCES

CROSS-REFERENCE TO RELATED APPLICATION

This application is a continuation of application Ser. No. 09/313,121, filed May 17, 1999, now U.S. Pat. No. 6,100,040, which is a continuation of application Ser. No. 08/739,069, filed Oct. 25, 1996, now U.S. Pat. No. 5,962,225 which claims priority to U.S. Provisional Patent Application No. 60/005,938, filed Oct. 27, 1995, entitled Diagnostic Procedures and Process for Detection of Specific DNA Sequences. These applications are herein incorporated, in their entirety, by reference.

TECHNICAL FIELD

The present invention comprises methods and compositions for detecting nucleic acid sequences. More particularly, the present invention comprises methods and compositions for detection of specific genetic sequences using nucleic acid target protection strategies. The methods and compositions of the present invention can be used in the detection of microorganisms, for diagnosis of infectious diseases in humans, animals and plants; assays of blood products, and for genetic analysis for use in such areas as early detection of tumors, forensics, paternity determinations, transplantation of tissues or organs and genetic disease determinations.

BACKGROUND OF THE INVENTION

Many target and signal amplification methods have been described in the literature, but none are believed to offer the combination of high specificity, simplicity, and speed. General reviews of these methods have been prepared by Landegren, U., et al., *Science* 242:229–237 (1988) and Lewis, R., *Genetic Engineering News* 10:1, 54–55 (1990). These methods include polymerase chain reaction (PCR), PCR in situ, ligase amplification reaction (LAR), ligase hybridization, Qβ bacteriophage replicase, transcription-based amplification system (TAS), genomic amplification with transcript sequencing (GAWTS), nucleic acid sequence-based amplification (NASBA) and in situ hybridization. Some of these various techniques are described below.

Polymerase Chain Reaction (PCR)

PCR is the nucleic acid amplification method described in U.S. Pat. Nos. 4,683,195 and 4,683,202 to Mullis. PCR consists of repeated cycles of DNA polymerase generated primer extension reactions. The target DNA is heat denatured and two oligonucleotides, which bracket the target sequence on opposite strands of the DNA to be amplified, are hybridized. These oligonucleotides become primers for use with DNA polymerase. The DNA is copied by primer extension to make a second copy of both strands. By repeating the cycle of heat denaturation, primer hybridization and extension, the target DNA can be amplified a million fold or more in about two to four hours. PCR is a molecular biology tool which must be used in conjunction with a detection technique to determine the results of amplification. The advantage of PCR is that it may increase sensitivity by amplifying the amount of target DNA by 1 million to 1 billion fold in approximately 4 hours. The disadvantage is that contamination may cause false positive results, or reduced specificity.

Transcription-based Amplification System (TAS)

TAS utilizes RNA transcription to amplify a DNA or RNA target and is described by Kwoh et al. (1989) *Proc. Natl. Acad. Sci., USA* 86:1173. TAS uses two phases of amplification. In phase 1, a duplex cDNA is formed containing an overhanging, single-stranded T7 transcription promoter by hybridizing a polynucleotide to the target. The DNA is copied by reverse transcriptase into a duplex form. The duplex is heat denatured and a primer is hybridized to the strand opposite that containing the T7 region. Using this primer, reverse transcriptase is again added to create a double stranded cDNA, which now has a double stranded (active) T7 polymerase binding site. T7 RNA polymerase transcribes the duplex to create a large quantity of single-stranded RNA.

In phase 2, the primer is hybridized to the new RNA and again converted to duplex cDNA. The duplex is heat denatured and the cycle is continued as before. The advantage of TAS over PCR, in which two copies of the target are generated during each cycle, is that between 10 and 100 copies of each target molecule are produced with each cycle. This means that $10^6$ fold amplification can be achieved in only 4 to 6 cycles. However, this number of amplification cycles requires approximately three to four hours for completion. The major disadvantage of TAS is that it requires numerous steps involving the addition of enzymes and heat denaturation.

Transcriptions Amplification (3SR)

In a modification of TAS, known as 3SR, enzymatic degradation of the RNA of the RNA/DNA heteroduplex is used instead of heat denaturation, as described by Guatelli et al. (1990) *Proc. Natl. Acad. Sci. USA* 87:1874. RNAse H and all other enzymes are added to the reaction and all steps occur at the same temperature and without further reagent additions. Following this process, amplifications of $10^6$ to $10^9$ have been achieved in one hour at 42° C.

Ligation Amplification (LAR/LAS)

Ligation amplification reaction or ligation amplification system uses DNA ligase and four oligonucleotides, two per target strand. This technique is described by Wu, D. Y. and Wallace, R. B. (1989) *Genomics* 4:560. The oligonucleotides hybridize to adjacent sequences on the target DNA and are joined by the ligase. The reaction is heat denatured and the cycle repeated. LAR suffers from the fact that the ligases can join the oligonucleotides even when they are not hybridized to the target DNA. This results in a high background. In addition, LAR is not an efficient reaction and therefore requires approximately five hours for each cycle. Thus, the amplification requires several days for completion.

Qβ Replicase

In this technique, RNA replicase for the bacteriophage Qβ, which replicates single-stranded RNA, is used to amplify the target DNA, as described by Lizardi et al. (1988) *Bio/Technology* 6:1197. First, the target DNA is hybridized to a primer including a T7 promoter and a Qβ 5' sequence region. Using this primer, reverse transcriptase generates a cDNA connecting the primer to its 5' end in the process. These two steps are similar to the TAS protocol. The resulting heteroduplex is heat denatured. Next, a second primer containing a Qβ3' sequence region is used to initiate a second round of cDNA synthesis. This results in a double stranded DNA containing both 5' and 3' ends of the Qβ bacteriophage as well as an active T7 RNA polymerase binding site. T7 RNA polymerase then transcribes the double-stranded DNA into new RNA, which mimics the Qβ. After extensive washing to remove any unhybridized probe, the new RNA is eluted from the target and replicated by Qβ replicase. The latter reaction creates $10^7$ fold amplification in approximately 20 minutes. Significant background may be formed due to minute amounts of probe RNA that is non-specifically retained during the reaction.

Chiron Signal Amplification

The Chiron system, as described by Urdea et al. (1987) *Gene* 61:253, is extremely complex. It utilizes 12 capture oligonucleotide probes, 36 labeled oligonucleotides, 20 biotinylated immobilization probes that are crosslinked to 20 more enzyme-labeled probes. This massive conglomerate is built-up in a stepwise fashion requiring numerous washing and reagent addition steps. Amplification is limited because there is no cycle. The probes simply form a large network.

ImClone Signal Amplification

The ImClone technique utilizes a network concept similar to Chiron, but the approach is completely different. The ImClone technique is described in Kohlbert et al. (1989) *Mol. and Cell Probes* 3:59. ImClone first binds a single-stranded M13 phage DNA containing targeted probe. To this bound circular DNA is then hybridized about five additional DNA fragments that only bind to one end and the other end hangs freely out in the solution. Another probe set is then hybridized to the hanging portion of the previous set of probes. The latter set is either labeled directly with an enzyme or it is biotinylated. If it is biotinylated, then detection is via a streptavidin enzyme complex. In either case, detection is through an enzyme color reaction. Like the Chiron method, the ImClone method relies on build-up of a large network. Because there is no repeated cycle, the reaction is not geometrically expanded, resulting in limited amplification.

While the nucleic acid amplification methods described above allow for the detection of relatively small quantities of target nucleic acid molecules, there is a need for the ability to detect target nucleic acid molecules in a shorter amount of time with less background interference. Problems inherent in PCR and other amplification techniques involve sample contamination during the collection techniques and the presence of amplicons (amplified target DNA). There are problems with non-specific target amplification mediated by closely related sequences and the production of primer dimers. There is also poor control of specificity, resulting in false positive reactions, and poor control of sensitivity, resulting in false negative reactions. PCR results must often be confirmed and validated by other techniques such as probe hybridization, Southern blotting or in situ hybridization.

Additionally, PCR and amplification techniques can only be used with very small amounts of starting sample DNA, in the range of a maximum of 1 microgram. This negates use of PCR techniques for the detection of low copy number nucleic acid targets. For example, early detection of HIV infection, soon after the initial viral infection, would be almost impossible to detect using PCR.

Thus, compositions, methods and kits are needed that are capable of detecting specific nucleic acid sequences and isolating them. Especially needed are methods and kits that would allow for the detection of low copy number nucleic acid target sequences. Additionally, there is need for methods and kits that provide the flexibility that would allow for isolation of nucleic acid sequences using a desired level of specificity.

What is also needed are methods that do not use amplification techniques, but do allow for the isolation of a specific target sequence from any amount of starting nucleic acid, especially large amounts, and have the flexibility to accomplish the isolation at several levels of specificity, depending on the level of specificity desired.

SUMMARY OF THE PRESENT INVENTION

In accordance with the present invention, methods and compositions are provided for the detection of specific nucleic acid sequences from cellular or tissue sources. More particularly, the present invention includes methods and compositions for the detection of nucleic acid sequences using a protection molecule that forms a protected nucleic acid sequence (PNAS) such as a triplex or duplex nucleic acid structure that includes the target nucleic acid sequence. The targent nucleic acid sequence is the specific sequence being detected. An assay using the methods of the present invention may include one, two or three levels of specificity to minimize false positive signals. An assay using the methods or compositions of the present invention can be performed on large amounts of purified DNA in a single test, with high levels of sensitivity, thus eliminating the need for in vitro DNA amplification procedures.

When the target nucleic acid sequence is double-stranded, the structure formed with the protection molecule is a triplex. When the target nucleic acid sequence is single-stranded, the structure formed with the protection molecule is a duplex. In this disclosure, where triplex structures are discussed, one can also substitute duplex structures or structures using PNA (peptide-nucleic acid) and the appropriate nucleases. Assays using the methods of the present invention may be referred to as TPA, Target Protection Assays.

The initial level of specificity utilizes protection molecules such as oligonucleotides or peptide-nucleic acids (PNA) to bind to specific target sequences of interest. Such binding may be accomplished by formation of Hoogstein-type hydrogen bonds. The protection molecule, bound to the target nucleic acid sequence, forms the protected nucleic acid sequence (PNAS). Once these PNAS structures are formed and stabilized in solution, the non-specific DNA is digested. For example, this digestion can be accomplished with a combination of endonucleases and a double-strand-dependent exonuclease, such as DNA Exonuclease III (Exo III). The endonucleases used in this example are designed to cut on both sides of the PNAS, leaving approximately 20 base pairs of DNA on each side of the sequence. Exo III, an exonuclease which progressively cleaves one strand of the DNA from the 3' end, is inhibited by the triple helix structure. Using a combination of nucleases, the unprotected DNA sequences are digested completely. A method of the present invention involving a lower level of specificity would employ an affinity molecule for capture and a reporter molecule for labeling in conjunction with the protection probe.

However, if a higher level of specificity is required, 5' flanking regions can be generated on either or both sides of the PNAS to allow for assays employing two further levels of specificity. The structure formed, a PNAS with flanking regions is termed PNAS/tail. Following the selected digestion around the PNAS, a capture probe, such as an oligonucleotide complementary to one of the single stranded flanking regions, is added. The capture probe is allowed to hybridize to a single-stranded region. For example, the capture probe could be an oligonucleotide that would bind to a single-stranded region and have an affinity molecule attached. For example, the affinity molecule could be didoxigenein or biotin. The capture probe comprises an affinity molecule and is capable of associating with the PNAS.

A capturing system is used to isolate the PNAS with the capture probe attached. Any capturing system that is capable of binding to the capture probe and separating the PNAS/tails with affinity molecule from the mixture is contemplated. In the example used above, such a capture system may comprise using magnetic beads coated with anti-didoxigenein antibodies for binding to the didoxigenein-capture probe portion or, streptavidin for binding to the biotin-capture probe portion. The PNAS/tails with affinity molecule, now attached to the magnetic beads, are separated from non-specific complexes and washed to remove any non-specific nucleic acid sequences. Such washing may use any washing technique known in the art. For example, a magnetic particle holder could be used. Again, should this be the level of specificity required, the present invention comprises assays that also have a reporter molecule associated with the protection molecule or the capture probe.

A third level of specific detection involves the addition of a labeled reporter probe. The reporter probe comprises a detectable label and is capable of associating with the PNAS. For example, the reporter probed may comprise an oligonucleotide complementary to the 5' single-stranded tail that is part of the PNAS/tail. This 5' region may or may not be on the opposite flanking tail to which the capture probe binds. The reporter probe may be labelled with any labels known in the art such as radioactivity or non-radioactive labels such as labeled with biotin or didoxigenein for indirect detection, or directly with a fluorescent reporter molecule, e.g., fluorescein, or chemiluminescent or bioluminescent labels. An excess of reporter probe is added to the washed magnetic bead-triplex complex and allowed to hybridize. Detection of the bound labelled reporter probe can be accomplished after washing by using detection devices specific for the type of label used. For example, if a fluorescent labeled reporter probe is used, the labeled sequences can be detected using a fluorometer or viewing the beads through a fluorescent microscope. Alternatively, the amount of bound probe can be directly assessed by fluorescent anisotropy with an analyzer such as the Abbott TDM analyzer.

Compositions of the present invention include compositions comprising the components to practice the methods taught herein. For example, a composition comprising a labeled protection molecule with an affinity molecule could be used in an assay with a first level of specificity. A composition comprising a labeled protection molecule and a capture probe could be used in a level two specificity assay. A composition comprising a protection molecule, a capture probe and a reporter probe could be used in a level three assay. It is to be understood that the individual molecules, probes and components can also be provided individually.

The present invention is especially useful for detecting specific genetic sequences. The present invention comprises methods such as the Target Protection Assay (TPA) in all its formats, which have the advantage of allowing the processing of very large amounts of purified nucleic acids, thus eliminating the need for artificial amplification procedures such as PCR, while enabling the detection of a specific target sequence. In addition, the three levels of specificity—PNAS formation, capture probe binding, and reporter probe binding—reduce technical problems such as those associated with false positive signals from non-specific amplification and/or hybridization.

The present invention comprises a method for detecting a target nucleic acid sequence, comprising obtaining isolated nucleic acid sequences from a sample suspected of containing a target nucleic acid sequence; contacting a protection molecule with the nucleic acid sequences under hybridizing conditions sufficient to form a PNAS; and detecting the PNAS. The methods may further comprise the steps of digesting the isolated nucleic acids containing one or more PNAS with nucleolytic enzymes to form a PNAS/tail; and hybridizing a capture molecule to the PNAS/tail; prior to the step of detecting the PNAS. Additionally, the methods may further comprise the step of hybridizing of a reporter molecule to the PNAS/tail; prior to the step of detecting the PNAS. A method for detecting specific nucleic acid sequences, comprising obtaining isolated nucleic acid sequences from a sample suspected of containing a target nucleic acid sequence; contacting a protection molecule with the nucleic acid sequences under hybridizing conditions sufficient to form a PNAS; digesting the isolated nucleic acids containing one or more PNAS with nucleolytic enzymes to form a PNAS/tail; hybridizing a capture molecule to the PNAS/tail; hybridizing of a reporter molecule to the PNAS/tail; and detecting the PNAS.

The present invention comprises compositions for detecting specific nucleic acid sequences, comprising a protection molecule capable of binding with a specific nucleic acid sequence. A composition of the present invention may further comprise a capture molecule. Additionally, a composition of the present invention may further comprise a reporter molecule.

The methods and compositions of the present invention should be ideal for the detection of viruses and other microorganisms such as pathogens of humans, animals and plants, as well as genetic analysis of polymorphic gene sequences such as HLA typing. The methods of the present invention can be used in forensics, paternity determinations, or transplantation or organs or tissues, or genetic disease analysis.

Accordingly, it is an object of the present invention to provide methods to detect specific genetic sequences.

It is yet another object of the present invention to provide methods for detecting specific DNA sequences involving triplex nucleotide structures.

It is another object of the present invention to provide methods for detecting specific RNA sequences involving triplex nucleotide structures.

It is yet another object of the present invention to provide methods for detecting specific DNA sequences involving duplex nucleotide structures.

It is another object of the present invention to provide methods for detecting specific RNA sequences involving duplex nucleotide structures.

It is another object of the present invention to provide methods for detecting specific RNA sequences involving PNA structures.

It is another object of the present invention to provide methods for detecting specific DNA sequences involving PNA structures.

It is yet another object of the present invention to provide methods for detecting specific DNA sequences involving antibodies.

It is yet another object of the present invention to provide methods for detecting specific RNA sequences involving antibodies.

Another object of the present invention is to provide a method of detecting nucleic acid sequences involving radioactive labeled nucleic acids.

It is another object of the present invention to provide a method of detecting nucleic acid sequences involving non-radioactive labeled nucleic acids.

It is yet another object of the present invention to provide a method of detection of specific genetic sequences with variable levels of specificity.

Another object of the present invention is to provide a method of detecting nucleic acid sequences for the determination of the identity of microorganisms.

It is another object of the present invention to provide a method of detecting nucleic acid sequences for the determination of the identity of human pathogens.

It is yet another object of the present invention to provide a method of detecting nucleic acid sequences for the determination of the identity of animal pathogens.

It is yet another object of the present invention to provide a method of detecting nucleic acid sequences for the determination of the identity of plant pathogens.

It is another object of the present invention to provide a method of detecting nucleic acid sequences for the determination of the genetic relationship, such as paternity or species identification, of a sample.

It is yet another object of the present invention to provide a method of detecting nucleic acid sequences for the determination of potential donors of organs or tissues for transplantation purposes or for protecting the blood supply.

It is another object of the present invention to provide a method of detecting nucleic acid sequences for use in forensic determinations.

It is yet another object of the present invention to provide a method of detecting nucleic acid sequences for the analysis of genetic diseases.

It is another object of the present invention to provide methods for testing body or tissue fluids to detect microorganisms or other pathogens.

These and other objects, features and advantages of the present invention will become apparent after a review of the following detailed description of the disclosed embodiments and the appended claims.

DETAILED DESCRIPTION

Figure 1:
FIG. 1 shows the steps of a method of the present invention. There are five individual steps in the TPA procedure as shown in FIG. 1: DNA isolation; PNAS formation, which in FIG. 1 is a triplex formation; endo/exonuclease digestion; addition of the capture probe with an affinity molecule, which in FIG. 1 is didoxigenein; isolation of the PNAS/tails with capture probe by addition of magnetic beads; addition of the reporter probe with its label, which in this case, the label is FITC (fluorescein isothiocyanate) and detection of the labeled PNAS/tail with reporter and capture probes.
Figure 1:
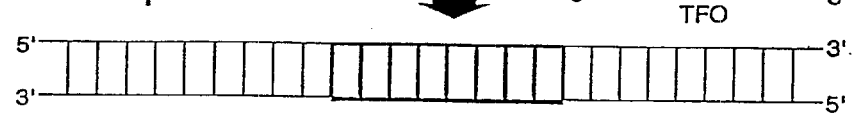
Figure 1:
Figure 1:
Figure 1:
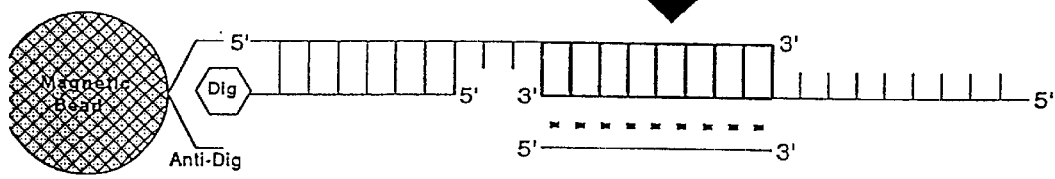
Figure 1:
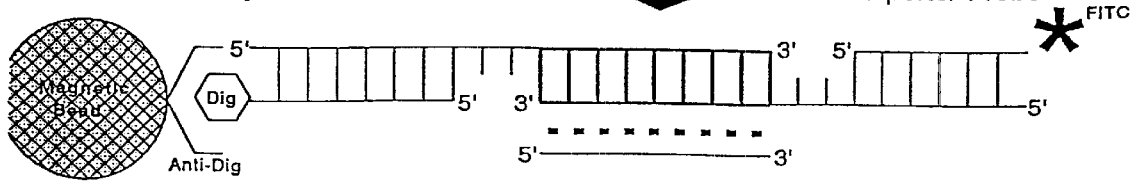

The present invention includes methods for the detection of a specific target nucleic acid sequence using a protection molecule that forms a protected nucleic acid sequence (PNAS) structure including the target nucleic acid sequence. An assay using the methods of the present invention may be referred to as TPA, target protection assay. One embodiment of the present invention is a method for the detection of specific DNA sequences. The present invention also includes methods for the detection of specific RNA sequences. In the disclosure herein, the nucleic acid DNA will be used but it is to be understood that any nucleic acid, including RNA, can be used with the methods of the present invention. Where specific nucleases are referred to, any nuclease that can perform the specified function can be substituted for the named nuclease.

The steps of a method of the present invention, the Target Protection Assay (TPA), involves the combination of several techniques to arrive at a unique nucleic acid diagnostic tool that is specific for a target nucleic acid seuqence. A preferred method of the present invention, directed at a DNA target nucleic acid, involves the steps of 1) DNA isolation; 2) formation of the PNAS; 3) enzymatic digestion of unprotected DNA; 4) capture; and 5) labeling and 6) detection of the PNAS.

Many of the individual procedures summarized herein may use techniques known to those skilled in the art of molecular biology, with several variations taught in the literature, or commercially available in the form of kits. It is to be understood that the present invention is not limited by the specifically disclosed techniques, but any techniques that are capable of performing the same function or result can be substituted for the ones described. For the purpose of example, a single technique will be described for each step in the TPA procedure. Suitable alternative techniques are noted where appropriate. However, the present invention is not to be limited thereby as many other suitable alternatives are intended to be included within the scope of the invention.

The present invention includes within its scope such nucleic acid targets as DNA (single and double stranded) and RNA (single and double stranded). The methods of the present invention are useful for specifically detecting the presence of very low copy number nucleic acid targets in a vast excess of non-target nucleic acids.

The methods of the present invention involve protecting the target, nucleic acid sequence from nuclease attack with the protection molecule, a molecule such as a single stranded DNA or RNA or a peptide nucleic acid (PNA). The protection molecule is selected or designed to bind specifically to the target nucleic acid sequence. The protection molecule, in association with the target nucleic acid sequence, forms a structure, the PNAS. For example, the PNAS includes, but is not limited to, triplex and duplex nucleic acid structures, peptide nucleic acid and antibody associated structures.

The methods of the present invention may include a protection molecule associated with an affinity molecule that allows binding of the PNAS in solution to a fixed substrate. The presence of the affinity molecule permits the removal of the excess extraneous nucleic acid. The methods of the present invention further involve a reporter molecule to permit visualization of the presence of the target nucleic acid.

An assay of the present invention that allows for the lowest level of specificity involves the binding of the protection molecule to the specific target nucleic acid sequence to form the PNAS. Diagnostic technologies are valuable only if they achieve high specificity (few false positives) and high sensitivity (few false negatives). In order to provide for a higher level of specificity, the present invention comprises methods wherein the target nucleic acid sequence is protected from nuclease attack when bound by the protection molecule to form the PNAS, and one or two enzymatically generated 5' DNA tails are generated, on one or both sides of the PNAS for hybridization with a capture probe containing an affinity molecule. The capture probe is selected or designed to specifically bind to a tail region of a tail-containing PNAS. This assay results in two levels of specificity-binding of the protection molecule and binding of the affinity molecule to the tail of the target nucleic acid. The affinity molecule allows for the attachment of the entire protection structure with the bound affinity molecule to be attached to a fixed substrate. In this example of an assay with two levels of specificity, either the affinity molecule or the protection molecule are labelled with any type of label known to those skilled in the art. The label would allow for detection of the PNAS having an affinity molecule.

A third level of specificity can be added to the assays contemplated by the present invention by generation of two different tail regions, preferably one on each side of the target nucleic acid, that extend beyond the target nucleic acid sequence bound by the protection molecule. The tail regions are included in the protected structure but are not bound to the protection molecule and the structure is named the PNAS/tails. One tail region could be bound to the capture probe to anchor the target to a fixed substrate (via the affinity molecule), and the other tail used to bind a reporter probe with label to visualize the presence of the nucleic acid target. The tail regions of the PNAS may or may not be necessary for use depending on the level of specificity desired. Preferably, the capture probe and the reporter probe are selected or designed to bind specifically and exclusively to one tail or the other, thereby ensuring that each of the two probes hybridizes to the PNAS/tail.

Increasing the number of levels of specificity increases the specificity of the assay (no false positives), however, excessive levels of specificity may decrease the levels of sensitivity generated (high false negatives). The present invention comprises assays that are dynamic diagnostic technologies that can be customized to deal with any specific nucleic acid target and yield any of a variety of desired levels of specificity.

Nucleic Acid Isolation

Nucleic acids may be isolated using any methods known to those skilled in the art. Nucleic acids, as used herein, means both DNA and RNA in all its forms found in cells or constructed by molecular biological techniques.

The method for DNA isolation used will largely depend on the amount and type of material to be extracted. Virtually any DNA isolation procedure reported in the literature which produces genomic or mitochondrial DNA, or any commercially available DNA isolation kit will suffice. The method contemplates that the sample amount of DNA to be used in each assay is concentrated in a volume that can range from 0.1 to 1.0 mL depending on the solubility of the DNA being tested. Larger DNA samples may require use of greater sized volumes. The methods of the present invention may test amounts of sample nucleic acids between picogram amounts to milligram amounts. The reactions components would have to be adjusted, for example, to provide adequate amounts for hybridization of the components. The reaction components are proportionate to not only the size of the sample tested but also to the relative number of target sequences that are present. It is to be understood that the amount of sample DNA will depend on the size and kind of sample.

The DNA is placed in a buffer suitable for the formation of PNAS, such as a duplex or triplex structure using a duplex or triplex forming oligonucleotide (DFO or TFO) or a peptide nucleic acid. Many procedures have been reported for the isolation of high molecular weight DNA from several sources including whole blood, isolated blood cells, serum and plasma, fresh, frozen or prepared tissues, and tissue culture cells.

RNA can also be isolated by any methods known to those in the art. Published RNA isolation protocols lyse the cell in a chemical environment that denatures ribonucleases, and fractionates the RNA type of interest from other RNAs and other cellular macromolecules. The RNA isolation method used is dependent upon the cell type from which the RNA is isolated and the eventual use of the RNA.

There are published methods for preparing total RNA from eukaryatic cells, and such methods are herein incorporated by reference. In Favaloco, et al., 1979 and Chomczynski and Sacchi, 1987, cells are lysed using guanidinium isothiocyanate. This method has few manipulations and yields clean RNA from many sources, and is the method of choice for tissues that have high levels of endogenous RNAse. In the third method of Palmiter, 1974, cells are lysed with phenol and SDS. This results in clean, high molecular weight RNA from large quantities of plant cells and also works well with some mammalian cells and tissues.

Published methods for preparing total RNA from prokaryotic cells include: protocols for extracting RNA from gram-negative and gram-positive bacteria, using protease digestion and organic extraction to remove protein and nuclease digestion to remove DNA (Reddy, et al., 1990); and a simple protocol for rapidly isolating RNA from *E.coli* without organic extractions, protease, or nuclease treatment (Summers, 1970). Lastly a published method (Aviv and Leder, 1972) can fractionate messenger RNA from ribosomal and transfer RNA based upon the exclusive presence of poly (A) tails on mRNA.

PNAS Formation

After isolation of the nucleic acid, the next step in the methods of the present invention include formation of the PNAS. This step introduces the first level of specificity to the assay. This step involves the formation of the PNAS using a target nucleic acid sequence-specific TFO or DFO or PNA. Hereinafter, TFO will be used in the example of a preferred embodiment, but it is to be understood that triplex and duplex structures and PNA are contemplated by the present invention.

The sequence of the TFO will depend on the specific target sequence to be detected. The most well characterized triplex structure is the one formed between a double stranded homopurine-homopyrimidine helix and a single stranded homopyrimidine tract. Formation of such structures are well known in the art. Specific details of the formation of such structures are given in the following references which are herein incorporated by reference. S. W. Blume, J. E. Gee, K. Shrestha, and D. M. Miller. Triple helix formation by purine-rich oligonucleotides targeted to the human dihydrofolate reductase promoter. *Nucl. Acids Res.* 20: 1777–1784 (1992).

In this first type of triple helix, the third homopyrimidine strand binds to the major groove, parallel to the homopurine strand of the Watson-Crick double helical DNA via Hoogstein hydrogen bonding. The third-strand thymidine (T) recognizes adenine-thymine (A:T) base pairs forming T:A:T triplets, and the third strand cytosine (C), protonated at the N-3 position, recognizes guanidine-cytosine (G-C) base pairs forming $C^+$:G:C triplets. Homopyrimidine oligonucleotide have been shown to form local triplexes with corresponding homopurine sites in larger double-stranded DNAs. An alternative triplex structure is a double stranded homopyrimidine-homopurine helix and a single stranded homopurine tract (TFO). Yet other alternative triplex structures comprise a combination of the two described structures.

The design of the TFO will generally follow the Pyrimidine-Purine-Pyrimidine binding rules described previously, or may be designed to form Purine-Purine-Pyrimidine triplexes if necessary. Such structures are well-known in the art. However, other binding motifs also apply, examples: I. Rec A Mediated TFO binding in 4 base regions (Rec A required to remain in solution); II. Triple purine and triple pyrimidine triplexes. Rec A is a recombinant enzyme that catalyzes the recombination between two DNA strands with similar homology.

While not wishing to be bound by the following theory, the premise of using TFOs to select specific regions of DNA for diagnostic use requires one to have a conserved sequence of DNA from the target sequence and to have a long enough sequence to ensure hybridization and selectivity. The human genome has approximately $5\times10^9$ base pairs of DNA. In order to have a unique sequence this would require an oligonucleotide of approximately between 16–20 nucleotides long. The actual number is probably smaller due to the presence of intron sequences in the DNA. Longer sequences increase the hybridization between the TFO and DNA while decreasing the specificity.

The selection of the TFOs is based on an empirical search for poly-purine/pyrimidine stretches in the target region. In the methods of the present invention, several confounding factors such as DNA/protein interactions should not interfere with the binding of the TFO to its target sequence. Also, secondary structure can be influenced by temperature, which should allow for more efficient TFO binding. Often the sequence is not entirely a homopurine strand but contains intermixed pyrimidines. Even though the introduction of pyrimidines could lower the TFO's affinity for the duplex DNA, the entire sequence still allows selective binding at the proposed hybridization temperature. The conditions to form the triplex structure may also vary depending on the target sequence, but must be compatible with the nucleases used in the subsequent step. For example, the conditions may need to be adjusted for activity by Exonuclease III (Exo III) and the restriction endonucleases chosen for the next step in the procedure (see next section).

To aid in the formation of a triplex structure, a low pH buffer (pH 6.8–7.4) would be optimal. This would also serve to help stabilize the structure during the enzymatic digestion step. Additional stabilization procedures, known to those in the art, can also be employed. For example, while TFOs may work well under a variety of situations, there are two fundamental problems unique to triplex formation. One is that, for the CT motif, acidic pH is required for triplex formation. The second is that the recognition sequence is limited to oligopurines. The first problem can be approached by altering the nucleic acid with chemical modifications, such as those taught in the art. See J. S. Lee, L. J. Woodsworth, P. Latimer, and A. R. Morgan. Poly (pyrimidine).poly(purine) synthetic DNA's containing 5-methylcytosine form stable triplexes at neutral pH. *Nucleic Acids Res.* 12: 6603–6614 (1984). This is done by replacing dC with modified bases such as 5-methyl-dC, C-5 propyne pyrimidine, 6-methyl-8-oxo-2'-deoxyadenosine, or 2'-O-methylpseudocystein.

Another approach is to add a linker to increase and stabilize the interaction with the target sequence. In an additional approach the TFO can also be conjugated to unique chemical groups to allow the formation of a triplex structure when it normally would not. Not only can triple-stranded DNA complexes be stabilized by a high ionic strength or by the presence of cations like magnesium, but also by triple-helix specific ligands called benzopyridoindole (BPI) derivatives, which intercalate in triple helix complexes. The present invention contemplates all of these methods that are well known in the art and other binding schemes that function in the same manner.

Lower pH conditions are compatible, although not necessarily optimal, with Exo III and most restriction endonucleases. In addition, these conditions allow triplex formation at the elevated temperatures (37° C.) needed for the subsequent digestion step.

An example of formation of a triplex structure is given here. A >10-fold molar excess of the TFO is added to the isolated DNA (10 pmoles TFO/µg DNA) and the triplex structure is allowed to form for 10 min. When the DNA and TFO are mixed in equal amounts, the kinetics of triplex formation has been characterized by half-decay times (t½) of 150–390 seconds. By contrast, when the TFO was in tenfold excess over the DNA the kinetics were faster and the t½ decreased to 19–28 seconds. The rate of triplex appears to be about three orders of magnitude slower than the rate of duplex recombination, which has a rate constant in the order of $10^6$. The apparent activation energy associated with the rate constant of triplex formation was small and negative ($E_1=26\pm15$ kJ/mol). The first order rate constant of triplex formation ($k_{-1}$) depends on temperature and was in the range of $10^{-7}$ to $10^{-5}{}_s{}^{-1}$ (at 20° C. and 33° C., respectively), with an apparent activation energy that was large and positive ($E_{-1}=355\pm33$ kJ/mol). The rate of triplex formation also showed a dependence on ionic strength (I) of the buffer solution (17,23,24). A decrease of I from 137 mM to 57 mM resulted in a six-fold decrease in the association constant.

Enzymatic Digestion of DNA

This step in the methods of the present invention assures that 5' tails of approximately at least 20 base pairs are generated upstream and downstream from the PNAS. These tails are useful for the capture and detection steps. This step also ensures that all non-specific nucleic acids are digested as well as unbound TFO, DFO and PNA molecules, thus reducing potential false-positive signals.

More specifically, once the PNAS is formed and stabilized, a mixture of exo- and endonucleases are added to the mixture. The endonucleases are sequence specific restriction enzymes chosen to flank the target nucleic acid site, leaving approximately 20 base pairs (usually more) of nucleic on each side. Where the target nucleic acid sequence is dsDNA, the exonuclease must be ds DNA dependent which digests only one strand (either 3' to 5' or 5' to 3'), leaving large tracts of ss DNA available for hybridization with specific probes. A preferred enzyme (and the one used in all examples) is Exo III. Exo III is a monomeric protein of 28,000 Daltons that catalyzes the stepwise 3' to 5' removal of 5'-mononucleotides from ds DNA with a free 3'-OH end. Exo III also contains an inherent 3' phosphatase activity and a RNAse H activity. Thus, Exo III can also be used in methods of the present invention that use RNA target sequences.

The enzymes shown in Table 1 may be used in the present invention. The present invention is not limited to the disclosed enzymes.

TABLE 1

Properties of some mammalian nucleases

| Enzyme | Substrate | Mode of action[1] | pH[2] | $Mg^{1+}$ | Reaction product[3] | Mol. wt. |
|---|---|---|---|---|---|---|
| DNAse I | ds/ss DNA | Endo | 7.1 | + | 5' oligos | 31 Kdal |
| DNAse II | ds/ss DNA | Endo | 4.1 | − | 3' oligos | 38 Kdal |

TABLE 1-continued

Properties of some mammalian nucleases

| Enzyme | Substrate | Mode of action[1] | pH[2] | Mg$^{1+}$ | Reaction product[3] | Mol. wt. |
|---|---|---|---|---|---|---|
| DNAse III | ss Duplex DNA | Exo | 8.5 | + | 5' monodinu-nudeotides | 52 Kdal |
| DNAse IV | Duplex DNA | Exo 3'5' | 8.5 | + | 5' mono | 42 Kdal |
| DNAse V | Duplex DNA | Exo 3'5'/5'3' | 8.8 | + | 5' mono | 12 Kdal |
| DNAse VI | ss DNA | Endo | 9.5 | + | 5' oligo | 45 Kdal |
| DNAse VII | ss and nicked & ds DNA | Exo 3'5' | 7.8 | + | 5' mono | 43 Kdal |
| DNAse VIII | 5' ss and nicked | Exo 5'3' | 9.5 | + | 5' oligos | 31 Kdal |
| Correxo | ss DNA nicked UV'd ds DNA[4] | Exo 3'5'/5'3' | 8.0 | + | 5' oligos | 30–35 Kdal |
| Lysosomal or spleen exonuclease | RNA or DNA with 5' OH | Exo 5'3' | 5.5 | − | 3' mono | 70 Kdal |

[1]Endo = endonucleolytic. Exo = exonucleolytic
[2]optimum pH
[3]Oligonucleotide shown is the main reaction product.
oligos = oligonucleotides
mono = mononucleotides
[4]UV irradiated double stranded DNA Exo III is commercially available from many sources at a reasonable cost, and will create the desired single stranded regions adjacent to the target DNA. Most importantly, Exo III will not digest dsDNA that is in a triplex structure, and thus the PNAS with the target sequence will be protected from digestion. One unit of Exo III will digest 50 ng of genomic DNA at 37° C. in 10 min. The main purposes of the endonucleases is to produce free ds DNA ends close to the TFO target site to aid the Exo III in digesting the genomic DNA and tail generation. Furthermore, endonuclease activity will increase the solubility of the sample DNA and complete digestion would eliminate nontarget DNA as a source of non-specific interactions. In some reactions, pre-treatment with noninterfering nucleases may be used to increase the nucleic acid solubility and help minimize the solution volume to be tested. This should allow the use of less Exo III than would be required to digest full length genomic DNA. In addition, complete endonuclease digestion is also not necessarily required to obtain the desired product.

In its simplest form, methods of the present invention can be fulfilled by this single protection step by concomitantly introducing a molecule for the capture system and a reporter molecule for target identification of the PNAS, yielding an assay with a single level of specificity. Additional nuclease steps may be necessary to prevent interference from unbound TFO and non-specific signals. In order to increase the level of the specificity, additional steps involving additional oligonucleotide probes can be added.

Oligonucleotide Probe—Capture System

Further steps in the methods of the present invention comprise the second level of specificity. These steps involve the hybridization of a capture probe containing an affinity molecule (such as biotin or digoxigenin) to the digested PNAS/tail and binding of the complex to a derivatized solid support (such as magnetic beads, microtiter plates, or membranes). This step allows greater sample manipulation because it can be used for concentration of the target sequences, buffer exchange, as well as removal of non-target nucleic acids.

The sequence of the capture probe will be complementary (Watson-Crick base pairing) to one of the ss (single-stranded) DNA regions flanking the PNAS which was generated by the nuclease digestion step. For example, a greater than 10-fold molar excess of the capture probe can be added to the PNAS/tail under conditions favoring specific hybridization. Such conditions are known to those skilled in the art. For example, 2.0M NaCl, 0.2 M sodium acetate, pH 4.5, 50° C., for 1 hour could be used. Following hybridization, the complexes will be purified by co-incubation with the derivatized solid support for an additional 1 hour under the same conditions, followed by adequate washing of unbound complexes (e.g. 8 times with hybridization buffer).

At this point, the complexes may be dissociated from the support, if desired, with a dissociation buffer. Such conditions are known to those skilled in the art. For example, 1.0 M Tris-HCl, pH 9, 0.5 mM EDTA for 20 min. could be used.

The options for affinity capture systems are numerous and are well known in the art. Such capture systems include, but are not limited to, the two most cited systems, biotin (capture with streptavidin) and digoxigenin (Dig, Boehringer-Mannheim, captured with anti-Dig antibody). However, any other similar system can be used.

In the case of solid supports, the situation is similar. The use of derivatized membranes (such as nylon) have had widespread application in the literature, and could be used in the present invention where detection using film exposure or phosphor imaging (such as with radioactivity or chemiluminescence) is desired. These supports also work well with the available enzyme conjugate systems (alkaline phosphatase [AP] or horseradish peroxidase [HRP]) with non-radioactive color producing substrates.

Another option for a solid support is a derivatized microtiter plate. These plates are available with many options from several sources. One advantage of microtiter plates is the availability of many supporting systems for automated manipulation (i.e. washing steps) and detection options (radioactivity, U.V. and visible light spectroscopy, and fluoresence). This system has the disadvantage of being limited to a relatively small volume (100–200 µl/well).

A system that is rapidly growing in popularity is the use of derivatized magnetic beads (Dynal). Non-magnetic beads (usually agarose or sepharose) have been used for affinity capture and purification for many years. The magnetic bead system is a preferred system for the manipulations needed for the methods of the present invention, and it will be the system used for the example here. These beads are available derivatized with both strepavidin and anti-Dig.

The assay could be completed at this point if this level of specificity is acceptable. The capture probe or protection molecule could be labeled so that the captured PNAS could be detected.

Oligonucleotide Probe Detection

The third level of specificity in the methods of the present invention is achieved through the use of a reporter probe. It is also at this step that the specific mechanism of detection is introduced. The reporter probe consists of a synthetic single stranded oligonucleotide complementary to the opposite single stranded end (not being used for attachment to the capture system) generated by the nuclease digestion. The composition of this detection step will vary depending on the method used. All methods of detection will require the presence of a reporter probe that be specifically detected as it binds to a specific sequence on the captured PNAS. For this invention the method need only be sufficiently sensitive to detect this specific probe-complex interaction so that a positive results can be defined.

The composition of the oligonucleotide probe will depend on the method of detection used. For direct detection of the probe, the probe may simply be a specific sequence of nucleotides complimentary to the specific sequence on the PNAS/tail where the interaction is detected by any physical method that can detect a specific interaction of oligonucleotides. An example of such a detection technique would be fluorescence anisotropy where the relative amount of bound probe can be measured directly without the removal of unbound probe.

In the case of fluoresence anisotropy, the relative level of bound probe can be measured directly without the removal of unbound probe. Methods based on separation might perturb the equilibrium binding of the probe and may led to erroneous results. In the use of anisotropy spectrophotometric determination, the concentration of free and bound material are measured by an observable change in the chromophore (i.e. due to changes in the molecular weight after hybridization). The fraction bound can be expressed as $f_b=(r_{obs}-r_{in})/(r_b-r_{in})$, where $f_b$ is the fraction bound, rin is the initial anisotropy, robs is the observed anisotropy after hybridization, and $r_b$ is the total binding (determined by titrating a small concentration of the probe with an excess of binding agent). With this information, the kinetics of binding can be seen for both small molecules and macromolecules. This methodology has been applied to observing oligonucleotide hybridization in solution, and is used in the TPA assay.

Other physical methods may include evenescent wave technology that detects changes in the physical properties of a surface as proteins or nucleic acids specifically interact on that surface. There are a number of related physical methods that can be used where the specific interaction can be measured without separation of bound and free labeled oligonucleotide.

Direct detection of the oligonucleotide probe can involve a specific sequence of nucleotides complimentary to the 5'tail on the PNAS/tail moiety where the oligonucleotide is derivatized with a label that can emit a signal when specifically bound to the target DNA Triplex. For the detection to be specific, any unbound directly labeled oligonucleotide would have to be separated from the bound form prior to detection. Examples of labels that can be directly incorporated into oligonucleotides include: radioactive isotopes, such as $^3H$, $^{14}C$, $^{32}P$, $^b$ $^{125}I$ that are detected using scintillation or gamma counters, fluorescent dyes that can be detected by fluorimeters, bioluminescent, chemiluminescent or electrochemiluminescent labels that can be detected using specific triggering reactions to generate light that can be quantified in a luminometer.

The various types of labels and methods of labeling nucleotide sequences are well known to those skilled in the art. Many of these labeling formats can be used in the above described assays with the first or second level of specificity. Several specific labels or reporter groups are set forth below.

For example, the label can be a radiolabel such as, but not restricted to, 32P, $^3H$, $^{14}C$, $^{35}S$, $^{125}I$, or $^{131}I$. A $^{32}P$ label can be incorporated into the sequence of the probe by nick-translation, end-labeling or incorporation of labelled nucleotide. A $^3H$, $^{14}C$ or $^{35}S$ label can be incorporated into the sequence of the probe by incorporation of a labelled precursor or by chemical modification. An $^{251}I$ or $^{131}I$ label can be incorporated into the sequence of the probe by chemical modification. Detection of a label can be by methods such as scintillation counting, gamma ray spectrometry or autoradiography.

The label can also be a Mass or Nuclear Magnetic Resonance (NMR) label such as, for example, $^{13}C$, $^{15}N$, or $^{19}O$. Detection of such a label can be by Mass Spectrometry or NMR.

Dyes and fluorogens can also be used to label the probes. Examples of dyes include ethidium bromide, acridines, propidium and other intercalating dyes, and 4',6'-diamidino-2-phenylindole (DAPI)(Sigma Chemical Company, St. Louis, Mo.) or other proprietary nucleic acid stains. Examples of fluorogens include fluorescein and derivatives, phycoerythrin, allo-phycocyanin, phycocyanin, rhodamine, Texas Red or other proprietary fluorogens. The fluorogens are generally attached by chemical modification. The dye labels can be detected by a spectrophotometer and the fluorogens can be detected by a fluorescence detector.

The probe can alternatively be labelled with a chromogen to provide an enzyme or affinity label. For example, the probe can be biotinylated so that it can be utilized in a biotin-avidin reaction which may also be coupled to a label such as an enzyme or fluorogen. The probe can be labelled with peroxidase, alkaline phosphatase or other enzymes giving a chromogenic or fluorogenic reaction upon addition of substrate. For example, additives such as 5-amino-2,3-dihydro-1,4-phthalazinedione (also known as Luminol™) (Sigma Chemical Company, St. Louis, Mo.) and rate enhancers such as p-hydroxybiphenyl (also known as p-phenylphenol) (Sigma Chemical Company, St. Louis, Mo.) can be used to amplify enzymes such as horseradish peroxidase through a luminescent reaction; and luminogeneic or fluorogenic dioxetane derivatives of enzyme substrates can also be used.

Recognition sites for enzymes, such as restriction enzyme sites, can also be incorporated into the probes to provide a detectable label. A label can also be made by incorporating any modified base or precursor containing any label, incorporation of a modified base containing a chemical group recognizable by specific antibodies, or by detecting any bound antibody complex by various means including immunofluorescence or immuno-enzymatic reactions. Such labels can be detected using enzyme-linked immunoassays (ELISA) or by detecting a color change with the aid of a spectrophotometer. It will be understood by those skilled in the art that other reporter groups can also be used.

Indirect detection of the oligonucleotide probe can involve a specific sequence of nucleotides complimentary to the specific sequence on the PNAS/tail where the oligonucleotide is derivatized with a reagent or entity that can be caused to produce a detectable signal in the presence of another specific reagent or entity. An example of an indirect detection system is the covalent derivatization of the oligonucleotide probe with a unique chemical structure that can be uniquely recognized by a binding partner; i.e., a hapten label such as biotin or digoxigenin or a unique piece of nucleic acid or nucleic acid related material where avidin, anti-digoxigenin, or a complimentary strand of nucleic acid itself is directly labeled and capable of detection by a physical method after removing any free label from specifically bound label. Another example of an indirect label is an oligonucleotide that is covalently derivatized with an enzyme that can convert a substrate into a detectable compound or release energy that can be detected by physical methods. Examples of enzyme-substrate pairs that can be used for indirect detection include:

1) Phosphatases such as alkaline phosphatase that can be detected by addition of phosphorylated compounds which when dephosphorylated by the result in compounds that, a) absorb light at a wavelength different form the substrate; b) can produce a specific fluorescence; c) become luminescent; d) become a substrate for a second enzyme that can be included with a second substrate to generate a detectable signal.

2) Peroxidases, for example, horseradish peroxidase, whose reaction products in the presence of appropriate compounds can generate compounds that, a) absorb light at a wavelength different form the substrate; b) can produce a specific fluorescence; c) become luminescent; d) become a substrate for a second enzyme that can be included with a second substrate to generate a detectable signal.

3) Luciferases that can be detected by addition of appropriate substrates and cofactors which result in the production of light. Alternatively, luciferases can be included as the second enzyme in assays where the substrate was a phosphorylated luciferin that is only acted upon by a luciferase after removal of the phosphate. Other hydrolytic enzymes other than the specific ones listed here can be used as indirect enzyme labels.

The methods of the present invention can be used to detect single copy or low copy number nucleic acid sequences from any size sample, including large amounts of nucleic acids. An unexpected benefit of the assays of the present invention resides in the ability to process large samples of nucleic acid and to detect and quantify specific nucleotide sequences that make up only a minor component of the complex mixtures of sequences in the large sample.

The sensitivity limits can be approximated by evaluation of available detection systems combined with the amount of target that can be obtained from a specific sample size. A very sensitive system for nucleic acid detection is a bioluminescence technique based on the photoprotein, AquaLite®. This technique is described in Actor et al., (1996) J. NIH Res. 8 (10):62, herein incorporated by reference in it entirety. The system is capable of detecting $3 \times 10^6$ specific sequences of DNA in a hybridization immunoassay technique with high signal to background noise ratio.

In the methods of the present invention, a bioluminescent conjugate of AquaLite®, coupled to an anti-digoxigenin antibody, is used to detect a digoxigenenin labeled reporter probe containing 2–3 digoxigenin molecules used in the methods of the present invention. At the present time, the lower limit of detection of the signal produced by the bioluminescence protein requires that there be $3 \times 10^6$ signals produced. Amplification systems, such as PCR would require amplifying a selected sequence to reach this level of detection. In contrast, using the methods of the present invention one could start with a large original sample that contains at least $3 \times 10^6$ specific sequences and detect them directly from the large sample.

The limiting step is the signal detection system, not the assay of the methods of the present invention. Other techniques may be used to provide lower limits of detection. With a signal amplification system in combination with TPA, single copy genes could be detected DNA samples from as little as 100 µl of a blood sample.

For example, a very early detection of infection with HIV could be made with the methods of the present invention. Without TPA, the earliest detection of HIV could not occur until the infected person produced antibodies to HIV, a period of 6 months after initial infection. Using TPA, the blood could be tested immediately after possible HIV infection by isolating all white blood cells via leucophoresis, then extracting the DNA, (approximately 5–8 mg DNA/500 mL of whole blood), assaying with methods of the present invention using a labeled reporter probe with 2–3 digoxigenin, and detecting the HIV sequences with AquaLite® coupled to an anti-digoxigenin antibody. Should there not be enough sequences for the signal detection system in the initial sample, subsequent blood samples could be taken and pooled because TPA can be employed with such a large sample size of nucleic acid. This testing procedure could provide very early detection of infection with HIV.

The present invention comprises a method for detecting a target nucleic acid sequence, comprising obtaining isolated nucleic acid sequences from a sample suspected of containing a target nucleic acid sequence; contacting a protection molecule with the nucleic acid sequences under hybridizing conditions sufficient to form a PNAS; and detecting the PNAS. The methods may further comprise the steps of digesting the isolated nucleic acids containing one or more PNAS with nucleolytic enzymes to form a PNAS/tail; and hybridizing a capture molecule to the PNAS/tail; prior to the step of detecting the PNAS. Additionally, the methods may further comprise the step of hybridizing of a reporter molecule to the PNAS/tail; prior to the step of detecting the PNAS. A method for detecting specific nucleic acid sequences, comprising obtaining isolated nucleic acid sequences from a sample suspected of containing a target nucleic acid sequence; contacting a protection molecule with the nucleic acid sequences under hybridizing conditions sufficient to form a PNAS; digesting the isolated nucleic acids containing one or more PNAS with nucleolytic enzymes to form a PNAS/tail; hybridizing a capture molecule to the PNAS/tail; hybridizing of a reporter molecule to the PNAS/tail; and detecting the PNAS.

The present invention comprises compositions for detecting specific nucleic acid sequences, comprising a protection molecule capable of binding with a specific nucleic acid sequence. A composition of the present invention may further comprise a capture molecule. Additionally, a composition of the present invention may further comprise a reporter molecule.

Procedure Variations in the Methods of the Present Invention

As discussed above, the methods of the present invention include a wide variety of alternative methods which can be substituted within each of the above described steps. An entire method could be performed in situ (using intact cells) and evaluated microscopically or in a flow cytometer. In addition, the steps themselves may also be modified to achieve the desired result. For example, Steps 2 (formation of the PNAS) and 3 (digestion of the extraneous nucleic acids) may be combined into a single procedure. This could be accomplished because the conditions that are described for the formation of the PNAS (Step 2) allow for rapid binding of the protection probe to its target sequence (see above for theory of triplex formation kinetics). As long as the formation of the protection structure is significantly faster than the digestion of the nucleic acid by the exonuclease (Step 3), there will still be complete protection of the protection structure with the target sequence. A lead time of at least approximately minutes for the formation in Step 2 was included to insure that the advantage went to the binding of the protection probe over that of enzymatic DNA digestion, however this may not be required in most cases.

In this respect, Steps 4 and 5 could also be combined into a single hybridization/capture step with no purification in between. Since each probe is unique to its own target sequence, there should be no danger of cross hybridization to produce false signals. This possibility is further reduced by the fact that each probe carries a different label (i.e. capture with Dig vs. reporter with FITC). Since the hybridization and wash procedures are identical in each step, combining the two would represent a significant simplification of the steps of the methods of the present invention. Ultimately the number of method steps is dependent on the desired level of specificity. Excessive steps may have a negative effect on sensitivity. Those skilled in the art would be well aware of the level of specificity desired and the level at which the assay should be performed.

The methods of the present invention are especially useful for detecting specific genetic sequences. The present invention comprises methods such as the Target Protection Assay (TPA), which has the advantage of allowing the processing of very large amounts (>1 mg) of purified DNA, thus eliminating the need for artificial amplification procedures such as PCR, while enabling the detection of single target sequences. In addition, the three levels of specificity—target protection, capture probe, and reporter probe—drastically reduce technical problems such as those associated with false positive DNA amplification and/or hybridization signals.

The methods of the present invention can be used for the detection of viruses and other microorganisms such as pathogens of humans and animals, as well as genetic analysis of polymorphic gene sequences such as with HLA typing. The methods of the present invention can be used for taxonomical purposes for cells, microorganisms, animals, plants or any other nucleic acid containing organisms. The isolation of specific nucleic acid sequences could be used for diagnosis of diseases found in humans, animals, plants or other organisms. The methods of the present invention can be used in forensics, paternity determinations, or transplantation or organs or tissues, or genetic disease analysis. Microbial nucleic acid sequences are defined at the nucleic acid sequences from microorganisms such as, but not limited to, viruses, bacteria, micoplasma, fungi, viroids, slow viruses, and scrapie-like organisms.

The methods of the present invention can be used for detection of nucleic acid sequences and thus are applicable to many uses. The following is a list of uses of the methods of the present invention:
Testing the blood supply to prevent the transmission of infectious agents
Detection of infectious agents in blood, blood products, and the organ-donor supply
Detection of HIV status early in the course of infection
Confirmation of diagnosis of pediatric AIDS
Diagnosis of hereditary disease
Early detection of infectious diseases from fluids or tissues of infected humans, animals and plants.
Early detection of tumor cells in normal tissues
Detection of type I diabetes during fetal development
Determination of drug resistance prior to administration of the drug
Forensic identity testing For example, the methods of the present invention can be used for the detection of nucleic acids in samples taken from bodily fluids and from environmental sources such as surfaces, air, or water. Because the methods of the present invention can isolate specific nucleic acid sequences from samples containing large amounts of nucleic acids, the source of the nucleic acid is not to be limited by the examples herein taught. Any source of nucleic acid can be employed with the methods of the present invention.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

General Format of Target Protection Assay Using A ds DNA Target Sequence with PNAS Mediated by Triplex Formation Isolation of DNA The following protocol is a representative procedure for the rapid isolation of DNA from large amounts of whole blood: 150 mL of blood collected in venipuncture tubes (heparin, ACD or EDTA) is pooled together and diluted with 150 ml Isoton II (Coulter Diagnostics) in a 500 ml centrifuge bottle. 30 ml of 10% Triton X-100 is added and mixed vigorously for 3 seconds. Cell nuclei are pelleted at maximum speed (12,000×g) for 5 minutes. After removal of the supernatant, the pellet is resuspended in 10 ml PK mixture (10 mM Tris-HCl, pH 8.0, 1 mM EDTA, 0.5% Tween 20, 0.5% NP-40, and 2.5 mg/ml Protease K), incubated at 55° C. for 15 min, 95° C. for 10 min (to inactivate the Protease K), and then slowly cooled to room temperature. The sample is then transferred to a centrifuge tube and spun at 12,000×g for 10 minutes. The supernatant is recovered and the DNA is pelleted with the addition of 0.2 volumes of 10M ammonium acetate and 2 volumes of ethanol. The precipitated DNA is pelleted at 5,000×g for 10 minutes, washed twice with 70% ethanol, and then resuspended in 0.5 ml sterile water. Mild sonication or shearing may be required to obtain complete dissolution of the pellet. Approximately 1 mg of total genomic DNA should be recovered from 150 ml whole blood (approx. 150 million nucleated cells). Any RNA preparative technique can also be applied.

Formation of PNAS Mediated by Triplex Formation

To the 0.5 ml DNA sample in water, add 50 $\mu$l 10×TFO buffer (0.25 M Tris-acetate, pH 7.0, 0.5 M NaCl, 100 mM MgCl$_2$, 50 mM-mercaptoethanol, 0.10 mg/ml BSA, and 40 mM spermine-HCl), followed by 10 nmoles of the specific TFO. Incubate for a period of time, and at a temperature sufficient to permit the formation of stable PNAS, for example at 37° C. for 10 min, before proceeding to the next step.

Enzymatic Digestion

Add 500 units of each restriction enzyme (50 $\mu$l in most cases) and 4,000 units of Exo III (40 $\mu$l of a 100,000 u/ml stock). Incubate the reaction at 37° C. for an additional 50 min, followed by inactivation of the enzymes by a biochemical or biophysical method. The sample is now ready for the next step in the procedure.

Capture System

To the digested DNA mixture, add 10 nmoles of Dig labeled capture probe and 0.5 ml 2.5×hybridization buffer (5.0 M NaCl, 0.5 M NaOAc, pH 4.5). Incubate the mixture at optimal hybridization temperature for a period of time sufficient to permit stable hybridization complexes to form, for example 1 hour, followed by the addition of 100 µl of anti-Dig coated magnetic beads, washed and resuspended in hybridization buffer. After an additional 1 hour incubation, isolate the beads using a magnetic particle concentrator and wash eight times with 0.5 ml hybridization buffer. The sample is now ready for the final step in the DNA triplex TPA procedure.

A FITC labeled reporter probe is used and detection is accomplished using fluorescence anisotropy. After the initial anisotropy of a 1.0 mL solution containing 10 nmoles of reporter prove in hybridization buffer is measured, it is added to the washed magnetic beads. The mixture is incubated for 1 hour at 50° C. with gentle rocking, followed by transfer of the entire contents (including beads) to an Abbott TDM sample vial. The anisotropy is then remeasured compared to the initial value for analysis. The fraction bound can be expressed as $f_b=(r_{obs}-r_{in})/(r_b-r_{in})$, where $f_b$ is the fraction bound, $r_{in}$ is the initial anisotropy, $r_{obs}$ is the observed anisotropy after hybridization, and $r_b$ is the total binding (determined by titrating a small concentration of the probe with an excess of binding agent).

EXAMPLE 2

HIV

Human immunodeficiency virus type 1 (HIV-1) is one of the two etiologic agents of AIDS. Currently, serologic assays which detect the presence of anti-HIV antibodies are used to screen blood and blood products.

While generally reliable, these tests will occasionally produce false positive results due to cross reactive antibodies or false negative results if the infection is at an early stage before the onset of a measurable immune response. It is in the latter case that alternative methods such as TPA (Target Protection Assay, a method of the present invention) may be particularly useful, since large amounts of sample DNA may be processed and tested in a single assay tube. A direct assay for the virus using co-cultivation with a susceptible cell line does exist, however this method is labor intensive and requires several days to complete. The following example will describe the extraction of a large amount of blood for the worst case: that of a recently infected individual with low levels of infected CD4 positive cells.

1. Extract DNA from 150 ml whole blood (150 million white cells) as described above in Example 1.
   Resuspend purified DNA in 0.5 ml water.
2. Add 50 µl 10×TFO buffer and 10 nmoles TFO:
   HIV-1 TFO (SEQ ID NO:1)
   5'-TTT TCT TTT CCC CCC T-3'
3. Incubate 10 min at 370° C.
4. Add 500 units Sau 3A and 4,000 units Exo III.
5. Incubate 50 min at 37° C., followed by 20 min at 60° C.
6. Add 0.5 ml 2.5× hybridization buffer and 10 nmoles of Dig labeled capture probe:
   HIV-1 Capture probe (SEQ ID NO: 2):
   5'-ACT GCC ATT TGT ACT GCT GT-Dig-3'
7. Incubate 50° C. for 1 hour.
8. Add 100 µl washed Dig coated magnetic beads.
9. Incubate 50° C. for 1 hour with rocking.
10. Place tube in a magnetic concentrator and remove liquid.
11. Wash 8× with 0.5 ml hybridization buffer.
12. Resuspend beads in 1.0 ml hybridization buffer containing 10 nmoles reporter probe previously measured for fluorescence anisotropy:
    HIV-1 reporter probe (SEQ ID NO: 3):
    5'-GAA TAG TAG ACA TAA TAG TA-FITC-3'
13. Incubate 50° C. for 1 hour.
14. Remeasure anisotropy and analyze fraction of bound probe ($f_b$) by the formula given above.

Alternatively, after step 13 the beads can be repurified with the magnetic particle concentrator, washed 8× with hybridization buffer, and placed in a fluorometer for direct fluoresence measurement ($-_{exc}$=490 nm, $-_{em}$=520 nm), or the beads can be placed on a slide for viewing on a fluorescent microscope.

EXAMPLE 3

Borrelia bergdorferi

The spirochete B. bergdorferi is the causative agent of Lyme disease. This agent is transmitted primarily through the bite of infected ticks, resulting in arthritic, neurological, and rheumatoid symptoms, making clinical diagnosis difficult. The primary tests for this agent are serologic and bacterial culture, both of which are relatively low in sensitivity, especially at the early stages of the disease. Sources of test material include whole blood, serum, joint fluid, cerebrospinal fluid, and urine. The following procedure is for 30 ml of whole blood:

1. Extract DNA from 30 ml whole blood (30 million white cells) as described above in Example 1. Resuspend purified DNA in 0.5 ml water.
2. Add 50 µl 10×TFO buffer and 2 nmoles TFO (SEQ ID NO: 4):
   TFO: 5'-TCC GCC TTT TGT TGT TTT TC -3'
3. Incubate 10 min at 37° C.
4. Add 100 units Ssp I, 100 units of Xho I, and 800 units Exo III.
5. Incubate 50 min at 37° C., followed be 20 min at 60° C.
6. Add 0.5 ml 2.5×hybridization buffer and 2 nmoles of Dig labeled capture probe:
   Capture probe (SEQ ID NO:5)
   5'-CCA GGC AAA TCT ACT GAA ACG CTG-Dig-3'
7. Incubate 50° C. for 1 hour.
8. Add 20 µl washed Dig coated magnetic beads.
9. Incubate 50° C. for 1 hour with rocking.
10. Place tube in a magnetic concentrator and remove liquid.
11. Wash 8× with 0.5 ml hybridization buffer.
12. Resuspend beads in 1.0 ml hybridization buffer containing 2 nmoles reporter probe previously measured for fluorescence anisotropy:
    reporter probe (SEQ ID NO:6):
    5'-TAG ACA AGC TTG AGC TTA AAG-FITC-3'
13. Incubate 50° C. for 1 hour.
14. Remeasure anisotropy and analyze fraction of bound probe ($f_b$) by the formula given above.

Alternatively, after step 13 the beads can be repurified with the magnetic particle concentrator, washed 8× with hybridization buffer, and placed in a fluorometer for direct fluorescence measurement ($-_{exc}$=490 nm, $-_{em}$=520 nm), or the beads can be placed on a slide for viewing on a fluorescent microscope.

EXAMPLE 4

B. dermatitidis

B. dermatitidis represents a family of fungal pathogens who's incidence of infection is increasing, especially among immunocompromised patients (such as organ transplant recipients). Current tests for fungal pathogens include serology and cultures, which are relatively slow and insensitive. A DNA-based test (non-PCR) has also been reported, but requires initial culturing of the pathogen before testing. The TPA procedure for this pathogen is identical to the previous examples with the following modifications: Isolate the DNA from 0.3 g wet yeasts or mycelia forms by the method of Lee and Taylor (39), and resuspend the isolated DNA in 0.5 ml water. Use 1 nmole of a TFO of (SEQ ID NO:7): of the sequence 5'-TTC CTC CGT CGT CCG CGC-3' in the triplex formation step. Use 100 units of Rsa I and Msp I, and 800 units of Exo III in the digestion step. Use 1 nmol of Dig labeled capture probe (SEQ ID NO:8) of the sequence 5'-GGT AGC CGT TTC TCA GGC TCC TC-Dig-3', and 50 µl Dig coated magnetic beads for capture. Finally, use 1 nmol of a reporter probe (SEQ ID NO:9) of the sequence 5'-GAG GTA GTG ACA ATA AAT ACT GAT-FITC-3' for the detection step.

EXAMPLE 5

Babesia microti

B. microti is a tick transmitted protozoal pathogen which infects humans and is found primarily in the U.S. This is the primary etiologic agent associated with the Nantucket fever outbreak off the coast of New England. Diagnosis is based mainly on serologic detection of anti-B. microti antibodies or the visualization of intraerythrocytic inclusions. The TPA procedure for this agent is identical to the above examples with the following modifications:
1. Extract DNA from 30 ml whole blood and resuspend in 0.5 ml water.
2. Use 2 nmoles of each probe at the appropriate step:
   TFO (SEQ ID NO: 10):
   5'-GGG GCG ACG ACG GGT GAC GGGG-3'
   Capture (SEQ ID NO:1):
   5'-TCT GAC CTA TCA GCT TTG GAC GGT-Dig-5'
   Reporter (SEQ ID NO:12):
   5'-TAG ATG TGG TAG CCG TTT CTC AGG-FIC-3'
3. Use 100 units of Xho I and Mun I, plus 800 units of Exo III for digestion.

EXAMPLE 6

Methicillin Resistant Staphylococcus aureus

Methicillin resistant strains of S. aureus were initially isolated soon after the drug was introduced for clinical use. Resistant strains produce a penicillin-binding protein with low affinity for–lactam antibiotics, thus rendering the pathogen resistant. This protein is produced by an acquired gene, mecA, which is the target for TPA detection (45). DNA is isolated from bacterial colonies growing on sensitivity disk agar (Nissui) by the method of Cassiday et al (46), or directly from blood or serum as described above. The following modifications will be used for the TPA procedure listed above for the drug resistant form of S. aureus:
1. Extract DNA from 30 ml whole blood and resuspend in 0.5 ml water.
2. Use 2 nmoles of each probe at the appropriate step:
   TFO (SEQ ID NO:13):
   5'-CCA TTT TTC CCT GAG CTT TTT-3'
   Capture (SEQ ID NO:14) Dig-5'
   5'-TAA TTC TTC AGA GTT AAT GGG A -Dig -5'
   Reporter (SEQ ID NO:15):
   5'-AAC ATG AAG ATO GCT ATC GTG TC -FITC -3'
3. Use 100 units of Sal I and Mnl I, plus 800 units of Exo III for digestion.

EXAMPLE 7

Assay Combinations

The following is a listing of combinations of target nucleic acids and protection molecules. The present invention is not limited to these examples and other combinations can be used by those skilled in the art.

| Target Nucleic Acid | Protection Molecule |
|---|---|
| ss DNA | ss DNA |
|  | ss DNA with crosslinkers |
|  | ss DNA that covers restriction sites with homologous bases/non-cross linking |
|  | ss DNA with crosslinkers and 5' non-homologous tail |
|  | ss RNA with crosslinkers |
|  | ss RNA with non-homologous RNA tail on either side of target |
|  | ss RNA with crosslinkers |
|  | ss RNA |
|  | ss RNA + Antibody to hybrid |
|  | ss RNA with non-complementary RNA tail (either one or both sides of target sequence)[1] |
|  | ss RNA with non-complementary RNA tail, 3' side target[1] |
| ss DNA | ss RNA with non-complementary RNA tail, 5' side target[1] |
|  | ss DNA extending beyond flanking regions and covering restriction sites[3] |
|  | ss DNA homologous to target site[3] |
|  | ss DNA complementary to target |
|  | ss RNA with non-complementary DNA tail (either one or both sides of target sequence)[1] |
|  | ss RNA with non-complementary |

| Target Nucleic Acid | Protection Molecule |
|---|---|
| | DNA tail, 3' side target[1] |
| | ss RNA with non-complementary DNA tail, 5' side target |
| | ss DNA with non-complementary RNA tail (either one or both sides of target sequence) |
| | ss DNA with non-complementary RNA tail, 3' side target |
| | ss DNA with non-complementary RNA tail, 5' side target |
| | ss DNA with non-complementary 5' DNA tail |
| | ss RNA + DNA |
| ss DNA | ss RNA with non-complementary RNA tail, 5' side target[1] |
| | ss DNA target specific only with TFO |
| | ss DNA with non-complementary 5' tail[2] |
| | ss RNA with non-complementary RNA tail on both sides of target + antibody to hydbrid |
| | ss RNA with non-complementary RNA tail on both sides of target |
| | ss RNA with non-complementary 5' tail[2] |
| | ss RNA with non-complementary 5' DNA tail |
| ds DNA | TFO DNA or RNA |
| | PNA |
| | PNA with non-complementary 5' DNA tail |
| | Sequence specific protein |
| ss RNA | PNA |
| | ss DNA + Antibody to DNA/RNA hybrid |
| | ss RNA[3] |
| | ss DNA[3] |
| | ss RNA with cross linkers |
| | ss Dna with cross linkers |
| ss RNA | Sequence specific protein |
| ds RNA | TFO (RNA) |
| | TFO (DNA) |
| | PNA |

[1]+ Antibody to DNA/RNA hybrid can also be used to aid in binding
[2]binding aided by pH and ionic strength
[3]PNA can also be added.

Location of Affinity Molecule

On the ss DNA probe
On ss DNA
On oligo homologous to upstream 5' DNA (target nucleic acid) tail
On oligo homologous to 5' probe (protection probe) tail
On ss RNA probe
On ss RNA
On oligo homologous to 5' DNA (target nucleic acid) tail generated
On oligo homologous to RNA (protection probe) tail
On oligo homologous to RNA tail
On ss RNA cross-inked probe
On antibody
On antibody used in capture system
On antibody to hybrid protection structure
On PNA (peptide-nucleic acid)
On TFO (triplex forming oligo)
On oligo complementary to 5' flanking region of target
On oligo complementary to 5' DNA probe tail
On oligo complementary to 5' flanking region of target
On oligo attached to PNA
On oligo attached to TFO (DNA/RNA)
On sequence specific protein Location of Reporter Molecule On ss DNA probe
On ss DNA
On oligo homologous to downstream 5' DNA tail
On oligo homologous to upstream 5' DNA tail
On oligo homologous to generated 5' DNA tail
On oligo homologous to 5' probe tail
On ssRNA
On ss RNA probe
On oligo homologous to RNA tail (probe)
On ss RNA crosslinked probe
On antibody
On antibody used in capture system
On antibody to hybrid protection structure
On PNA (protein-nucleic acid)
On TFO (triplex forming oligo)
On oligo complementary to 5' flanking region of target
On oligo complementary to 5' DNA probe tail
On oligo complementary to 5' flanking region of target
On oligo attached to PNA
On oligo attached to TFO
On sequence specific protein Antibodies to the hybrid protection structure of DNA/RNA, either DNA target with RNA protection probe, or RNA target with DNA protection probe, can be used as a capture system. Peptide Nucleic Acid (PNA) can be used in the second hybridization step.

Triplex Forming oligonucleotides (TFO) can be used in the second hybridization step.

It should be understood, of course, that the foregoing relates only to preferred embodiments of the present invention and that numerous modifications or alterations may be made therein without departing from the spirit and the scope of the invention as set forth in the appended claims.

It is claimed:

1. A method for detecting a nucleic acid sequence associated with a disease, comprising:
   a) obtaining isolated unlabeled nucleic acid sequences from a sample suspected of containing the nucleic acid sequence;
   b) contacting at least one target-protecting molecule that specifically binds to the nucleic acid sequence with the isolated unlabeled nucleic acid sequences of step a) under hybridizing conditions sufficient to form at least one protected nucleic acid sequence (PNAS);
   c) digesting the PNAS of step b) with enzymes to form at least one PNAS structure having at least one 5' single-stranded region generated by enzymatic digestion (PNAS/tail);
   d) hybridizing a reporter probe to the at least one PNAS/tail of step c) wherein the reporter probe binds to a single-stranded region of the at least one PNAS/tail; and
   e) detecting the at least one PNAS/tail as indicative of the presence of the nucleic acid sequence associated with the disease.

2. The method of claim 1, further comprising, hybridizing a capture probe that specifically binds to a single-stranded region of at least one PNAS/tail, prior to the step of detecting the at least one PNAS/tail.

3. The method of claim 1, wherein the nucleic acid sequence is isolated from a human, animal, plant, or microorganism.

4. The method of claim 1, wherein the disease is cancer, type I diabetes, HIV, AIDS, pediatric AIDS, a hereditary disease, lyme disease or an infectious disease.

5. The method of claim 1, wherein the isolated nucleic acid sequence bound by the at least one target-protecting molecule is a sequence of an organism which causes disease.

6. The method of claim 5, wherein the organism is a microorganism, pathogen, virus, bacteria, mycoplasma, fungi, viroid, slow virus, or scrapie-like organism.

7. The method of claim 1, wherein the isolated nucleic acid sequence bound by the at least one target-protecting molecule is a sequence encoding an antibody or a fragment thereof.

8. A method for diagnosing a disease, comprising:
   a) obtaining a sample from a human, other animal, plant, or other organism suspected of having a disease;
   b) obtaining isolated unlabeled nucleic acid sequences from the sample;
   c) contacting at least one target-protecting molecule that specifically binds to the isolated unlabeled nucleic acid sequences of step b) under hybridizing conditions sufficient to form at least one protected nucleic acid sequence (PNAS);
   d) digesting the PNAS of step c) with enzymes to form at least one PNAS structure having at least one 5' single-stranded region generated by enzymatic digestion (PNAS/tail);
   e) hybridizing a reporter probe to the at least one PNAS/tail of step d) wherein the reporter probe binds to a single-stranded region of the at least one PNAS/tail; and
   f) detecting the at least one PNAS/tail as indicative of the disease.

9. The method of claim 8, further comprising, hybridizing a capture probe that specifically binds to a single-stranded region of at least one PNAS/tail, prior to the step of detecting the at least one PNAS/tail.

10. The method of claim 8, wherein the disease is cancer, type I diabetes, HIV, AIDS, pediatric AIDS, a hereditary disease, Lyme disease or an infectious disease.

11. The method of claim 8, wherein the isolated nucleic acid sequence bound by the at least one target-protecting molecule is a sequence of an organism which causes disease.

12. The method of claim 11, wherein the organism is a microorganism, pathogen, virus, bacteria, mycoplasma, fungi, viroid, slow virus, or scrapie-like organism.

13. The method of claim 8, wherein the isolated nucleic acid sequence bound by the at least one target-protecting molecule is a sequence encoding an antibody or a fragment thereof.

14. A method for detecting a polymorphism, comprising:
   a) obtaining isolated unlabeled nucleic acid sequences from a sample suspected of having at least one polymorphism;

b) contacting at least one target-protecting molecule that specifically binds to the isolated unlabeled nucleic acid sequences of step a) under hybridizing conditions sufficient to form at least one protected nucleic acid sequence (PNAS);

c) digesting the PNAS of step b) with enzymes to form at least one PNAS structure having at least one 5' single-stranded region generated by enzymatic digestion (PNAS/tail);

d) hybridizing a reporter probe to the at least one PNAS/tail of step c) wherein the reporter probe binds to a single-stranded region of the at least one PNAS/tail; and e) detecting the at least one PNAS/tail as indicative of the at least one polymorphism.

15. The method of claim 14, further comprising, hybridizing a capture probe that specifically binds to a single-stranded region of at least one PNAS/tail, prior to the step of detecting the at least one PNAS/tail.

16. The method of claim 14, wherein the sample is from a human, other animal, plant, or other organism.

17. The method of claim 14, wherein the method distinguishes between more than one polymorphism.

18. The method of claim 14, wherein the method is for HLA typing.

* * * * *

SEQUENCE LISTING

<160> NUMBER OF SEQ ID NOS: 15

<210> SEQ ID NO 1
<211> LENGTH: 16
<212> TYPE: DNA
<213> ORGANISM: Artificial Sequence
<220> FEATURE:
<223> OTHER INFORMATION: HIV-1 Triplex Forming Oligonucleotide

<400> SEQUENCE: 1
ttttcttttc ccccct                                                          16

<210> SEQ ID NO 2
<211> LENGTH: 20
<212> TYPE: DNA
<213> ORGANISM: Artificial Sequence
<220> FEATURE:
<223> OTHER INFORMATION: DIG labelled HIV-1 Capture Probe

<400> SEQUENCE: 2
actgccattt gtactgctgt                                                      20

<210> SEQ ID NO 3
<211> LENGTH: 20
<212> TYPE: DNA
<213> ORGANISM: Artificial Sequence
<220> FEATURE:
<223> OTHER INFORMATION: FITC labelled HIV-1 Reporter Probe

<400> SEQUENCE: 3
gaatagtaga cataatagta                                                      20

<210> SEQ ID NO 4
<211> LENGTH: 20
<212> TYPE: DNA
<213> ORGANISM: Artificial Sequence
<220> FEATURE:
<223> OTHER INFORMATION: Triplex Forming Oligonucleotide

<400> SEQUENCE: 4
tccgcctttt gttgttttc                                                       20

<210> SEQ ID NO 5
<211> LENGTH: 24
<212> TYPE: DNA
<213> ORGANISM: Artificial Sequence
<220> FEATURE:
<223> OTHER INFORMATION: DIG labelled Capture Probe

<400> SEQUENCE: 5
ccaggcaaat ctactgaaac gctg                                                 24

<210> SEQ ID NO 6
<211> LENGTH: 21
<212> TYPE: DNA
<213> ORGANISM: Artificial Sequence
<220> FEATURE:
<223> OTHER INFORMATION: FITC labelled Reporter Probe

<400> SEQUENCE: 6
tagacaagct tgagcttaaa g                                                    21

<210> SEQ ID NO 7
<211> LENGTH: 18

```
<212> TYPE: DNA
<213> ORGANISM: Artificial Sequence
<220> FEATURE:
<223> OTHER INFORMATION: Triplex Forming Oligonucleotide

<400> SEQUENCE: 7
ttcctccgtc gtccgcgc                                                 18

<210> SEQ ID NO 8
<211> LENGTH: 23
<212> TYPE: DNA
<213> ORGANISM: Artificial Sequence
<220> FEATURE:
<223> OTHER INFORMATION: DIG labelled Capture probe

<400> SEQUENCE: 8
ggtagccgtt tctcaggctc ctc                                           23

<210> SEQ ID NO 9
<211> LENGTH: 24
<212> TYPE: DNA
<213> ORGANISM: Artificial Sequence
<220> FEATURE:
<223> OTHER INFORMATION: FITC labelled Reporter probe

<400> SEQUENCE: 9
gaggtagtga caataaatac tgat                                          24

<210> SEQ ID NO 10
<211> LENGTH: 22
<212> TYPE: DNA
<213> ORGANISM: Artificial Sequence
<220> FEATURE:
<223> OTHER INFORMATION: Triplex Forming Oligonucleotide

<400> SEQUENCE: 10
ggggcgacga cgggtgacgg gg                                            22

<210> SEQ ID NO 11
<211> LENGTH: 24
<212> TYPE: DNA
<213> ORGANISM: Artificial Sequence
<220> FEATURE:
<223> OTHER INFORMATION: DIG labelled Capture Probe

<400> SEQUENCE: 11
tctgacctat cagctttgga cggt                                          24

<210> SEQ ID NO 12
<211> LENGTH: 24
<212> TYPE: DNA
<213> ORGANISM: Artificial Sequence
<220> FEATURE:
<223> OTHER INFORMATION: FITC labelled Reporter Probe

<400> SEQUENCE: 12
tagatgtggt agccgtttct cagg                                          24

<210> SEQ ID NO 13
<211> LENGTH: 21
<212> TYPE: DNA
<213> ORGANISM: Artificial Sequence
<220> FEATURE:
<223> OTHER INFORMATION: Triplex Forming Oligonucleotide

<400> SEQUENCE: 13
```

```
ccatttttcc ctgagctttt t                                    21
```

```
<210> SEQ ID NO 14
<211> LENGTH: 22
<212> TYPE: DNA
<213> ORGANISM: Artificial Sequence
<220> FEATURE:
<223> OTHER INFORMATION: DIG labelled Capture Probe

<400> SEQUENCE: 14
taattcttca gagttaatgg ga                                   22

<210> SEQ ID NO 15
<211> LENGTH: 23
<212> TYPE: DNA
<213> ORGANISM: Artificial Sequence
<220> FEATURE:
<223> OTHER INFORMATION: FITC labelled Reporter Probe

<400> SEQUENCE: 15
aacatgaaga tggctatcgt gtc                                  23
```